United States Patent [19]

Jaasma

[11] Patent Number: 4,724,700
[45] Date of Patent: Feb. 16, 1988

[54] DIFFERENTIAL FLOW GAS ANALYZER
[75] Inventor: Dennis R. Jaasma, Blacksburg, Va.
[73] Assignee: Center for Innovative Technology, Herndon, Va.
[21] Appl. No.: 830,266
[22] Filed: Feb. 18, 1986
[51] Int. Cl.⁴ .............................................. G01N 25/56
[52] U.S. Cl. ....................................................... 73/29
[58] Field of Search ................................. 73/29, 28, 23
[56] References Cited
U.S. PATENT DOCUMENTS 3,229,502 1/1966 Pappas et al. ............................ 73/29
4,507,875 4/1985 Hirsch et al. ......................... 73/29 X

FOREIGN PATENT DOCUMENTS 842536 6/1981 U.S.S.R. ................................... 73/29

Primary Examiner—Stewart J. Levy
Assistant Examiner—Joseph W. Roskos
Attorney, Agent, or Firm—Reed Smith Shaw & McClay

[57] ABSTRACT

The disclosure relates to a method for continuously measuring the concentration of water in a gas stream. Several stations are utilized to perform the measuring function and to particularly determine the amount of moisture in the sample gas stream. The gas sample is extracted from a duct and initially condensed at a relatively lower temperature to further extract heavy organic materials. The gas stream is then subjected to a first orifice in a heated oven to measure the gas flow before water vapor has been condensed out. After this measuring step the gas is subjected to an ice bath and a drying column to extract the water vapor from the gas sample. The flow rate dried gas sample is again measured by an orifice in a controlled environment. The molar flow rates can be compared to determine the water concentration of the flue gas.

19 Claims, 2 Drawing Figures

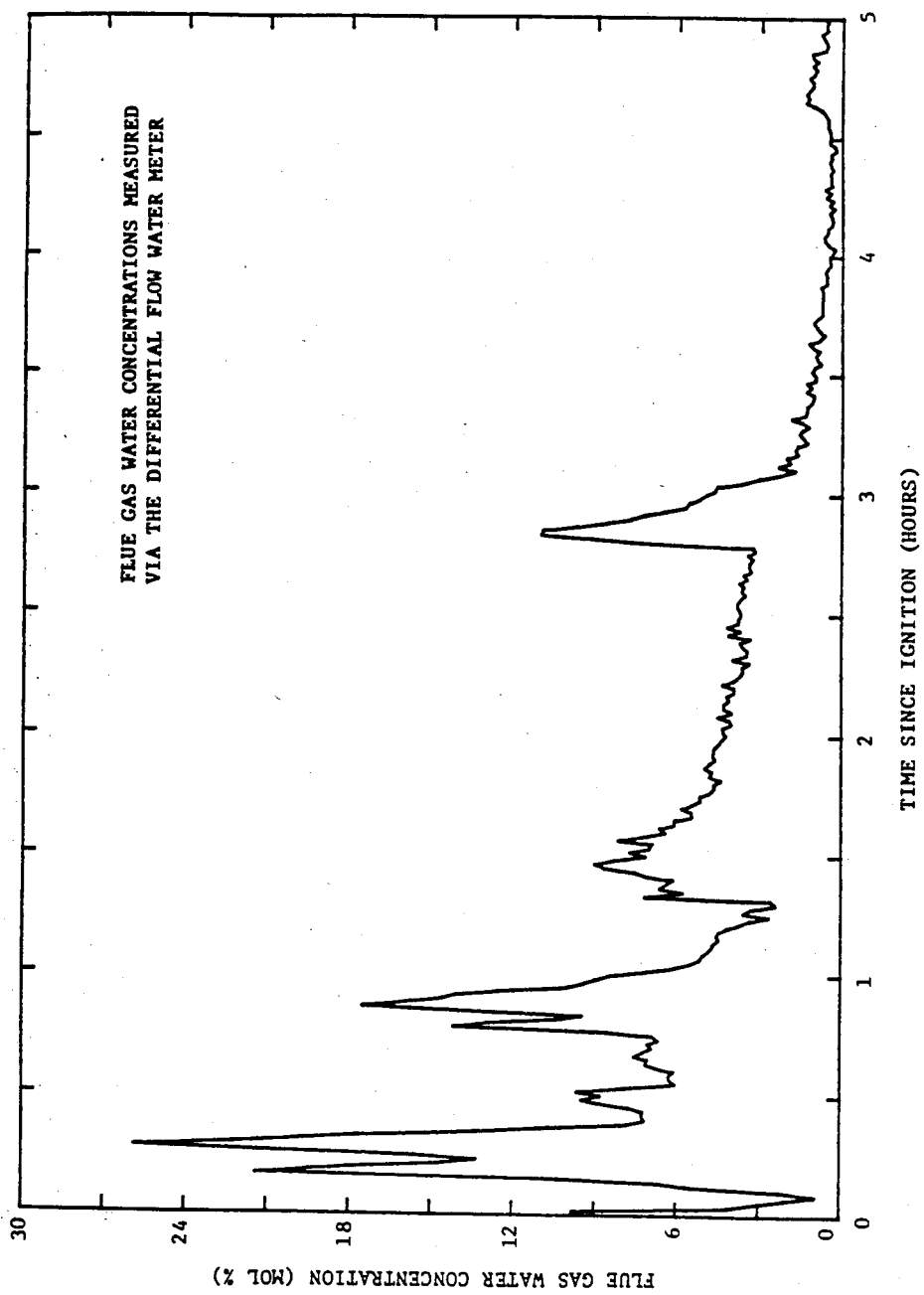

DIFFERENTIAL FLOW GAS ANALYZER

BACKGROUND AND DISCUSSION OF THE INVENTION

Conventional gas analyzers have been used to continuously measure the concentration of water or other condensable material in a gas stream. By measuring the types and quantities of gases in an exhaust gas stream of a boiler, one can determine the efficiency of the boiler in burning to completion all the fuel that is being used. By measuring the sensible energy content and chemical energy content of materials remaining in the flue gas and comparing that with the amount of the fuel actually used in the boiler one can evaluate the overall efficiency of the boiler as a heat-producing device.

Whether it is in the context of boiler efficiency or simply an environment where the amount of condensable fluid is a parameter which should be measured, various methods have been proposed for this type of analysis. For example, in the U.S. Pat. No. 3,229,502 to Pappas et al, issued on Jan. 18, 1966, there is disclosed a gas condensation pressure analyzer. The device disclosed relates to a process for determining the concentration of a selected condensable component of gas. The analyzer relies on the measurement of the total pressure required for condensation equilibrium between the sample gas and the condensed component at constant temperature conditions. The system to accomplish this includes a control valve that causes the total gas pressure to oscillate so as to cause a partial pressure of the analytically desired component to seek its vapor pressure. In the Pappas et al. system condensation is accomplished within a restriction or capillary maintained at a constant temperature by a cold bath. The sample gas is delivered directly to the constant temperature bath through a control valve, and once cooled the gas exits the bath through a discharge line.

Another example of a system for determining concentration of vapors in a flowing stream is U.S. Pat. No. 4,507,875, issued to Hirsch et al., on Apr. 2, 1985. The Hirsch et al. patent discloses an apparatus for determination of concentration of water vapor in the exhaust air of a drier used to dry tobacco. The system includes a gas evacuation conduit for receiving a sample of gas from the stream, a gas condenser in the evacuation conduit for condensing out essentially all condensable vapors in the sample and a gas flow meter connected to the gas discharge of the gas condenser for determining the flow of dry gas sample exiting the condenser. The vapor concentration determination is accomplished by sampling a gas line and directing the sample to a condenser, an electric compressor, kept at a temperature of about 5° C. so that the condenser will condense out all of the components of the flow of process gas.

Systems of the type discussed above suffer from many deficiencies. For example, it is often difficult to obtain an accurate measure of the flow rate due to materials existing in the gas which adversely affect the flow measuring equipment. Furthermore, the measuring steps are not conducted in a manner which insures that only flow rates of the desired materials are measured and that unwanted condensation is not obtained. The environment in which the measurements are made is not controlled sufficiently to provide reliable readings. Particularly where comparative readings are involved absence of controlled environments can adversely affect any comparison.

The invention described herein overcomes many of the problems which occur in the systems described above. For example, the sample is drawn initially through a first oven where organics and other materials are condensed and filtered out before the sample is directed to a measuring device. After this initial filtering step the sample is raised to a higher temperature in a second oven to insure that no further condensing occurs when an orifice is used to measure the flow rate of the material before it is subjected to a component removal system which could be an absorption system or a condensing system such as an ice bath. After having the component of interest removed the gas sample is again passed through a second orifice in the same oven as the first orifice to measure the flow rate of the remaining gas. These flow rates are compared to arrive at a percentage of water or other material within the gas. The gas can then be directed through a conventional dry basis gas analyzer to analyze the amount of various remaining components in the gas.

BRIEF DESCRIPTION OF THE DRAWINGS

FIG. 2 is a graph of flue gas water concentration against time.

DETAILED DESCRIPTION OF THE PREFERRED EMBODIMENT

Figure 1:
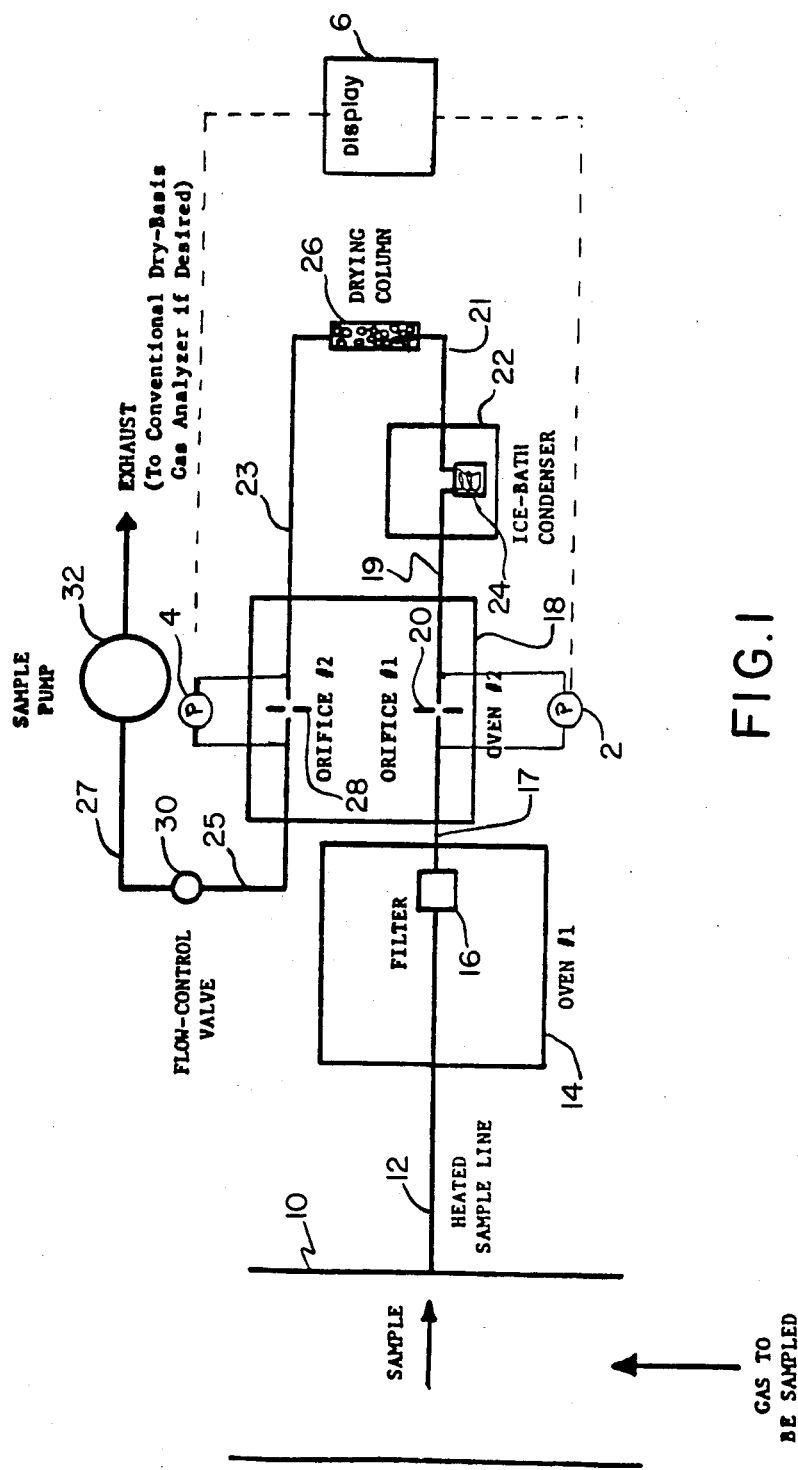
FIG. 1 is a schematic diagram of the method of the invention.

This embodiment measures the water content of the exhaust of a wood burning stove. As can be seen in FIG. 1 the system includes a flue or duct 10 which provides a source of the gas to be analyzed, also referred to as "stack flow", which in this case is connected to a wood stove. The stack flow moves at a flow rate dependent upon the amount of heat generated in the stove, the ability of air to flow into the oven, the length and size of duct or flue 10, and the height of the stack above ground level. In the specific embodiment of the method shown, the gas flow in flue 10 is a wet stack flow which also has condensable organics such as tar and creosote at a temperature typically in the range of 100°–400° C. A sample is drawn from flue 10 through a heated sample line or conduit 12 where the heated sample gas flow is directed to the first station, oven 14, for condensation and filtering of organic materials. As the sample is drawn from flue 10, often the temperature will be reduced due to the heat transfer between conduit 12 and surrounding atmosphere, and to avoid condensation of water in the line, the line is heated to 100° C. The first oven 14 is maintained at a temperature of 70° C., which, although higher than ambient, is substantially less than the temperature of the gas flowing through flue 10. As a result certain materials, such as tar and creosote, will condense out at this temperature. A filter is located in the conduit 12 within oven 14 to extract the particulate matter and particularly the tar and creosote condensed in this oven 14 prior to the measuring apparatus. As a consequence the gas exiting oven 14 in conduit 17 is substantially devoid of any particulate matter which is to be subjected to a measuring step.

A second station or oven 18 is maintained at about 80° C. or 10° above the temperature of oven 14. This second oven provides the station for measuring the flow rate of the gas delivered to oven 18 from the first station or oven 14. For measuring the fluid flow a sharp-edged orifice 20 is provided within oven 18 in the gas conduit. The requisite pressure measuring device 2 is employed in the conventional manner to measure the pressure on either side of orifice 20 and thereby measure the flow rate therethrough. The sample gas is then directed through conduit 19 out of oven 18 to a third station which is a condenser 22 for condensing out the water vapor. In this particular embodiment the condenser includes a coil submerged in the ice bath in container 24. The gas is subjected to the ice bath temperature for a sufficient length of time while flowing through the coil to substantially condense all the water in the gas. Other methods of condensing can be employed such a refrigeration units, pressure control devices, heat exchangers etc. Any apparatus is acceptable for this purpose so long as the temperature is not reduced to such a point that significant amounts of other materials will be condensed out along with the water. In some instances this may not be satisfactory, but in this particular embodiment the temperature should be set such that only the water and a negligible amount of organic material is condensed.

After having been subjected to the condenser 22 the gas is delivered through conduit 21 to a drying column 26 where any remaining moisture flowing with the gas is removed by a chemical attraction technique. In this particular case the drying column includes calcium sulfate which readily attracts moisture in the gas and is a well known drying substance for this purpose. Depending on the substance to be removed other materials could be employed in the drying column.

After having been dried the gas sample is then delivered through conduit 23 to a fourth station when the gas flow rate can be again measured. In this embodiment conduit 23 is connected to a second sharp-edged orifice 28 in oven 18, the same oven in which first orifice 20 appears. The measuring step at orifice 28 is accomplished, in a manner similar to that orifice 20, by a pressure measuring apparatus which measures the pressure of the gas both upstream and downstream of the orifice. These pressure measuring apparatus 2 and 4 are connected to electrical readout device 6 to provide an instantaneous measure of the flow rate at each orifice and to compare the flow rate if that should be desired. Downstream of the oven 18 conduit 25 connects the orifice 28 to flow control valve 30; in turn the conduit 27 connects the flow control valve 30 to sample pump 32. The pump 32 and flow control 30 cooperate to establish the flow rate of the gas sample from the flue 10 and ultimately to the exhaust line 29 as shown. With this system the water concentration of the flue gas is available as real-time quantity given by the following formula:

$$\% H_2O = 100 * \frac{\dot{n}_1 - \dot{n}_2}{\dot{n}_1}$$

In the formula, $\dot{n}_1$ and $\dot{n}_2$ are the molar flow rates before and after the drying process respectively. The same type of system can be used for measuring other gases if an absorbent (e.g., Ascarite for $CO_2$) for the gas of interest is substituted for the drying system of the example discussed herein.

Using this system, the amount of water concentrate can be determined over a preselected time period. FIG. 2 is a graph of water concentration vs. time for the flue gas water content of a wood-burning stove. The stove employed was made of sheet metal with a fire box volume of about 1.5 cubic feet ($ft.^3$) and is manufactured by Jackes-Evans. The sample line temperature was maintained at about 128° C. The first oven 14 was maintained at a temperature of about 70° C. while the second oven 18 was maintained at a temperature of about 87° C. The dry gas flow rate at the second orifice 28 was about 0.5 liters per minute. Under these conditions the pressure drop across the first orifice was maintained between about 0.8 and 1.25 inches of water and about 1.6 inches of water pressure drop across the second orifice.

The use of two ovens is a feature of the system which insures that the gas flow rates as measured are relatively accurate. The first oven permits condensation and removal of organic compounds with dew points between 70° C. and the flue gas temperature. Reheating the gas to 80° C. or more insures that no materials will condense in the second oven, where the orifices are located. If condensation occurred in the first orifice or the second orifice, the discharge coefficient of the orifice would change, and the molar flow rates would not be accurately known.

The above has been a description of the preferred embodiment. It should be understood that the full scope of the invention is defined by the claims which follow and any equivalents. Accordingly, there are modifications, improvements, and variations of the embodiment which may provide some differences but still come within the scope of the invention.

I claim:

1. A method for measuring the concentration of condensable matter in a gas comprising:
   (a) drawing a sample of the gas to be measured from a source of gas;
   (b) condensing said gas sample at a first station to remove vapors having a dew point between the temperature of said first station and the temperature of the source of gas;
   (c) filtering particulate matter in said first station including material condensed during said condensing step;
   (d) measuring the flow rate of said sample at a second station at a temperature greater than that of the condensing step at said first station;
   (e) condensing said sample to extract condensable matter at a third station at a temperature lower than that of the condensing step of said first station; and
   (f) measuring the flow rate of said sample at a fourth station at a temperature greater than that of said condensing step of said third station.

2. The method according to claim 1 wherein said condensing step at said third station includes cooling said sample sufficiently to condense the water from the gas sample.

3. The method according to claim 2 wherein said cooling step at said third station includes subjecting said sample to an ice-bath condenser.

4. The method according to claim 3 further comprising drying said gas sample after said condensing step at said third station to remove water remaining in the sample.

5. The method according to claim 4 wherein said subjecting said gas sample to an ice-bath condenser includes passing said sample through a coil immersed in an ice-bath.

6. The method according to claim 5 wherein said drying step includes passing said sample through a vapor absorbing material.

7. The method according to claim 6 wherein said measuring step at said second station includes passing said sample through a first sharp-edged orifice.

8. The method according to claim 7 wherein said measuring step occurring after said condensing step at the third station includes passing said sample through a second sharp-edged orifice.

9. The method according to claim 8 wherein both said measuring steps are accomplished within the same second station.

10. The method according to claim 9 wherein said second station is maintained at a temperature about 10° greater than that of said first station.

11. A method for determining the percentage of water in a gas comprising:
    (a) continuously drawing a sample of gas from a source;
    (b) passing said sample through a first oven maintained at a temperature below that of said gas source to condense out of the sample gas organics and passing said gas stream through a filter to remove condensate and other particulate;
    (c) passing said sample through a second oven maintained at a temperature sufficiently greater than that of said first oven to avoid any condensation and measuring the flow rate of said sample;
    (d) delivering the sample to an ice bath where the sample gas is continuously passed through a conduit of sufficient dimensions immersed in an ice bath to condense substantially all the water in the sample;
    (e) drying said sample to withdraw moisture in the sample by a chemical attraction process; and
    (f) passing said sample through said second oven and measuring the flow rate of said sample; and
    (g) comparing the flow rate of said sample prior to said condensing step in said ice bath with the flow rate subsequent thereto to determine the amount of water in the sample.

12. A method for measuring the concentration of condensible matter in a gas comprising;
    (a) drawing a sample of the gas to be measured from a source of gas;
    (b) condensing said gas sample at a first station to remove vapors having a dew point between the temperature of said first station and the temperature of the source of gas;
    (c) measuring the flow rate of gas sample at a second station at a temperature of 10° C. greater than that of the condensing step at said first station, said measuring step including passing said gas sample through a first sharp-edged orifice;
    (d) condensing said sample to extract condensible matter at a third station at a temperature lower than that of the condensing step of said first station by passing said sample through a coil immersed in an ice-bath;
    (e) drying said gas sample after the condensing step of the third station by passing said sample through a vapor absorbing material;
    (f) measuring the flow rate of said sample after said drying step by second sharp-edged orifice located in said second station.

13. The method according to claim 12 wherein said second station maintained at about 80° C.

14. The method according to claim 13 wherein said first station is maintained at about 70° C.

15. The method according to claim 14 wherein said first station includes a filter to filter out particulates condensed therein.

16. The method according to claim 15 wherein said sample is continuously drawn from a gas source.

17. The method according to claim 16 wherein said source is a gas flue connected to a stove.

18. The method according to claim 17 wherein said stove is wood burning stove.

19. The method according to claim 18 wherein said particulate includes organic compounds having a dew point between the temperature in the first station and gas flue.

* * * * *